United States Patent [19]

Schlegel

[11] Patent Number: 4,673,406
[45] Date of Patent: Jun. 16, 1987

[54] ONE-PIECE IMPLANTATION LENS

[75] Inventor: Hans-Joachim Schlegel, Bad Homburg, Fed. Rep. of Germany

[73] Assignee: Inprohold Establishment, Vaduz, Liechtenstein

[21] Appl. No.: 792,114

[22] Filed: Oct. 28, 1985

[30] Foreign Application Priority Data

Oct. 29, 1984 [DE] Fed. Rep. of Germany ....... 3439551

[51] Int. Cl.$^4$ .............................................. A61F 2/16
[52] U.S. Cl. ...................................................... 623/6
[58] Field of Search ............................ 623/6; 351/161

[56] References Cited

U.S. PATENT DOCUMENTS

| | | | |
|---|---|---|---|
| 4,010,496 | 3/1977 | Neefe | 623/6 |
| 4,074,368 | 2/1978 | Levy, Jr. et al. | 623/6 |
| 4,210,391 | 7/1980 | Cohen | 351/161 |
| 4,242,762 | 1/1981 | Tennant | 623/6 |
| 4,424,597 | 1/1984 | Schlegel | 623/6 |

FOREIGN PATENT DOCUMENTS 2124500 2/1984 United Kingdom .................... 623/6

Primary Examiner—Ronald L. Frinks
Attorney, Agent, or Firm—Erwin S. Teltscher; Peter R. Ruzek

[57] ABSTRACT

A one-piece implantation lens is provided as a replacement for a natural lens which has been surgically, particularly extracapsularly, removed from the eye of living beings of a higher order and which has, on the one hand, a central lens body designed as a collective lens and, on the other hand, holding means in the form of thin-walled, flat support elements arranged peripherally on the lens body, radially extending outwardly from the lens body and fixing it in place, with the outer edge of the support elements lying on a circular arc around the center of the lens body; and which consists of a homogenous, crystal-clear, high-temperature resistant plastic, preferably vulcanized silicone, with a specific gravity of between 1.01 and 1.08, preferably approximately 1.02, wherein at least one of the two surfaces of the central lens body is in the form of the optically effective surface of a Fresnel lens.

16 Claims, 12 Drawing Figures

ONE-PIECE IMPLANTATION LENS

BACKGROUND OF THE INVENTION

This invention refers to a one-piece implantation lens as a replacement for a natural lens which has been surgically, particularly extracapsularly, removed from the eye of living beings of a higher order and which has, on the one hand, a central lens body designed as a collective lens and, on the other hand, holding means in the form of thin-walled, flat support elements arranged peripherally on the lens body, radially extending outwardly from the lens body and fixing it in place, with the outer edge of the support elements lying on a circular arc around the center of the lens body; and which consists of a homogenous, crystal-clear, high-temperature resistant plastic, preferably vulcanized siliconematerial, with a specific gravity of between 1.01 and 1.08, preferably approximately 1.02.

Implantation lenses of the type described above have already proven their excellence in practical ophthalmology.

The wish has been expressed to be able to fold the lenses of the type in question, which consist of a flexible material, in order to enable them to be inserted into the eye through as small an incision as possible, of only a few millimeters in length, after the natural, clouded lens has been extracapsularly removed. On the one hand, it is necessary that the material of the implantation lens be relatively soft and flexible, but stiff enough to guarantee stability of form of the lens, yet on the other hand, the lens should be foldable for the reasons given above. However, the foldability of lenses with a corresponding thickness of the central lens body is limited in view of the required refracting power.

SUMMARY OF THE INVENTION

In order to do justice to all requirements set, the suggestion for the solution of the problems is to design the implantation lens in question such that at least one of the two surfaces of the central lens body is designed in the manner of the optically effective surface of a Fresnel lens, i.e. the lens is compiled of individual peri-axial ring zones with steps provided between them. The radii of curvature of the individual zone areas are selected such that the focal points of all zones coincide. It is thereby possible to provide a lens with relatively thin walls, to substantially reduce its volume and to achieve an appreciable reduction in weight. But in particular, lenses with this design can be more easily folded to reduce their width in the folded state to approximately one-half of the original width.

BRIEF DESCRIPTION OF THE DRAWINGS

Further features of the implantation lenses according to the invention can be found in the subclaims and the following description of a number of preferred embodiments, which are shown in FIGS. 1 to 12 of the drawings.

DETAILED DESCRIPTION OF THE DRAWINGS

Figure 1:
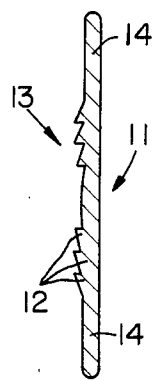
FIGS. 1 to 8 each show a cross section through one of various embodiments of the implantation lens according to the invention.

The implantation lens according to FIG. 1 consists of a flat plate of crystal-clear, flexible material, with a central lens body 11 arranged in the center thereof; the front of this lens body consists of the stepped ring zones 12 of a Fresnel lens 13. The rear of the lens body 11 is flat, for instance. The lens comprises a single piece. The support elements 14 are arranged on the periphery of the central lens body.

Figure 2:
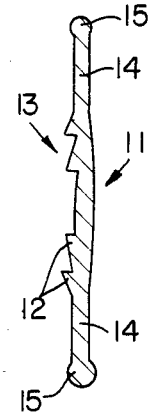

The lens according to FIG. 2 corresponds with that of FIG. 1 but in this figure the rear side of the central lens body 11 is convex. A rounded annular bulge 15 is located on the outer periphery of the support elements 14 to enlarge the contact surface on the sensitive tissue and to reduce the surface pressure.

Figure 3:
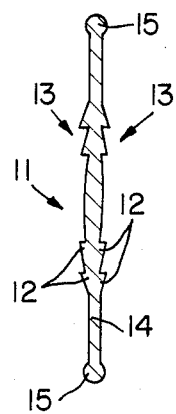
Figure 4:
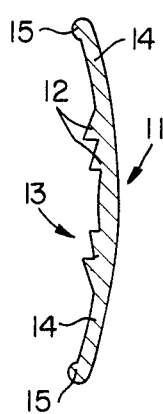

In the lens according to FIG. 3, the two surfaces of the central lens body 11 are provided with stepped rings 12. The lens according to FIG. 4 is curved toward the rear across its entire length. The front surface of the central lens body 11 consists of stepped rings 12 of a Fresnel lens.

Figure 5:
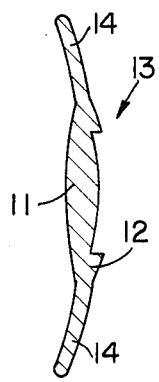
Figure 6:
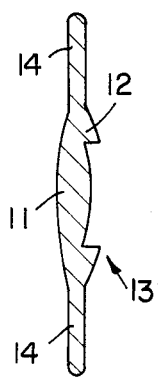
Figure 7:
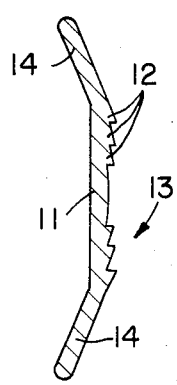
Figure 8:
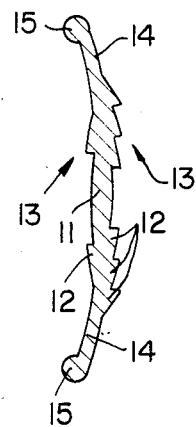
Figure 9:
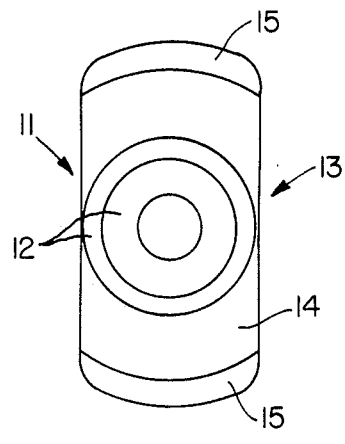
FIGS. 9 to 12 show plan views of implantation lenses according to FIGS. 1 to 8 with different outlines.
Figure 10:
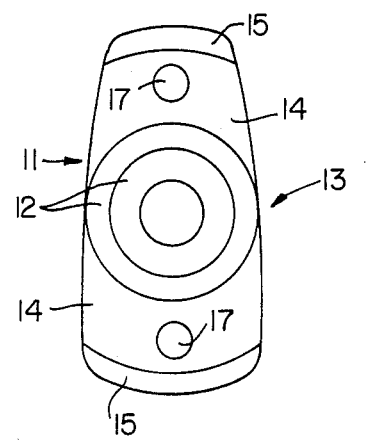
Figure 11:
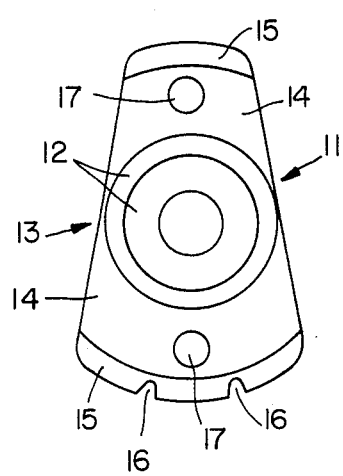
Figure 12:
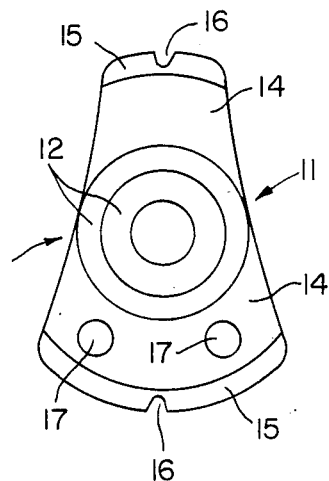

The implantation lenses according to FIGS. 5 and 6 show a biconvex central lens body 11, with a stepped rear surface. In the case of FIG. 5, the implantation lens is curved and in the case of the embodiment according to FIG. 6 it is straight. In the implantation lens according to FIG. 7 the central lens body 11 consists of a plano-convex lens with a stepped rear convex surface. The support elements 14 are angled toward the front relative to the central lens body 11. The embodiment of the implantation lens according to FIG. 8 corresponds essentially to that of FIG. 7. In this case the central biconvex lens body 11 is stepped both in the front and in the rear. The support elements 14 are also provided with an outer peripheral annular bulge 15.

The use of the embodiments of the implantation lens according to FIGS. 5 to 8 as a posterior chamber lens has the advantage that the posterior capsule still present in the eye can not abut the central rear surface of the implantation lens, as it is held at a desired distance from the lens by the backwardly projecting steps in the lens. The intermediate space thereby formed is important in the event that subsequent cataract formation occurs on the posterior chamber, which can then be broken up by a Yag laser without damaging the implantation lens at the same time.

In FIGS. 9 to 12 embodiments of the implantation lens are shown, wherein the central lens bodies can be provided with steps 12 as shown in FIGS. 1 to 8.

Implantation lenses in which the lower edge of the lower support element 14 is equipped with an annular bulge 15 and in which the lower edge is wider than the diameter of the central lens body, have the advantage that the contact surface which the tissue abuts is larger than the contact surface on the upper edge, so that the frequently observed rotation of the implantation lens in the eye can be avoided. If applicable, one or two notches 16 can be provided in the lower edge of the annular bulge 15, in order to counter the tendency of the lens to rotate.

All of the above-described and shown lenses offer the advantage of being extraordinarily light and flat, so that, if desired, they can also be folded to enable them to be inserted through the smallest possible incision in the cornea upon removal of the clouded lens, into the anterior chamber, or if applicable into the posterior chamber.

If the stepping of the lens rings 12 is selected such that the individual ring zones of the Fresnel lens lie below the focussing capability of the eye, they are no longer perceived as rings and therefore act in the same way as a lens with a continuously curved surface.

It is advantageous to provide openings 17 in the support elements 14, through which fluid from the chambers can pass and which facilitate the folding of the lens.

I claim:

1. A one-piece implantation lens for use as a replacement for a natural lens which has been surgically, in particular extracapsularly, removed from the eye of a living being of a higher order, comprising
   (a) a central lens body consisting of a homogenous, crystal-clear flexible plastic material with a specific gravity of between 1.01 and 1.08 and resistant to high temperatures,
   said lens body being delimited, as considered in the implanted position of the lens, by respective front and back major surfaces at least one of which has a configuration of a Fresnel lens having a circular central portion and at least one annular portion immediately surrounding said central portion,
   said central portion being offset from said annular portion into said lens body to reduce the thickness of said lens body and facilitate folding thereof during the implantation of the lens into the eye, and
   said major surfaces being so configured that said lens body has light-collecting properties and the light passing through both said central portion and said annular portion is focused into the same focal point, and
   (b) holding means including thinwalled, flat supporting elements arranged on the periphery of said lens body and extending radially outwardly therefrom for fixing said lens body in place upon implantation,
   said holding means having an outer edge lying on a circular arc around the middle point of said lens body.

2. The implantation lens according to claim 1, wherein said one major surface is said front major surface of said central lens body.

3. The implantation lens according to claim 1, wherein said one major surface is said back major surface of said central lens body.

4. The implantation lens according to claim 1, wherein the other of said major surfaces of said lens body is planar.

5. The implantation lens according to claim 1, wherein the other of said major surfaces of said lens body is convex.

6. The implantation lens according to claim 1, wherein said central portion of said one major surface of said lens body is planar.

7. The implantation lens according to claim 1, wherein said central portion of said one major surface of said lens body is convex.

8. The implantation lens according to claim 1, wherein said support elements are inclined relative to said lens body.

9. The implantation lens according to claim 1, wherein said support elements include an upper support element and a lower support element which has a wider peripheral contact and support surface than said upper support element.

10. The implantation lens according to claim 1, wherein said support elements include an upper support element and a lower support element; and wherein at least said lower support element is provided with a peripheral bulge.

11. The implantation lens according to claim 10, wherein said peripheral bulge includes at least one notch.

12. The implantation lens according to claim 10, wherein said support elements include at least one opening.

13. The implantation lens according to claim 1, wherein said specific gravity of said material of said lens body is approximately 1.02.

14. A one-piece implantation lens for use as a replacement for a natural lens which has been surgically, in particular extracapsularly, removed from the eye of a living being of a higher order, comprising
   a central lens body consisting of a homogenous, crystal-clear flexible plastic material with a specific gravity of between 1.01 and 1.08 and resistant to high temperatures, said lens body being delimited, as considered in the implanted position of the lens, by respective front and back major surfaces which are so configured that said lens body has light-collecting properties, with said front major surface having a configuration ranging from planar to slightly convex and said back major surface having a configuration of a Fresnel lens with a circular central portion and at least one annular portion immediately surrounding and backwardly offset from said central portion to reduce the thickness of said lens body and facilitate folding thereof during implantation of the lens into the eye, and said major surfaces being so configured that said lens body has light collecting properties and light passing through both said central portion and said annular portion is focused into the same focal point; and
   holding means including thin-walled, flat supporting elements arranged on the periphery of said lens body and extending radially outwardly therefrom for fixing said lens body in place upon implantation, said holding means having an outer edge lying on a circular arc around the middle point of said lens body.

15. The implantation lens according to claim 14, wherein said back surface of said lens body further has an additional annular portion immediately surrounding and backwardly spaced from said one annular portion.

16. The implantation lens according to claim 15, wherein said back surface of said lens body further has a further annular portion immediately surrounding and backwardly spaced from said additional annular portion.

* * * * *